United States Patent [19] [11] 4,423,525
Vallana et al. [45] Jan. 3, 1984

[54] HEART VALVE PROSTHESIS

[75] Inventors: Franco Vallana; Gioachino Bona, both of Turin, Italy

[73] Assignee: Sorin Biomedica S.p.A., Saluggia, Italy

[21] Appl. No.: 313,843

[22] Filed: Oct. 22, 1981

[30] Foreign Application Priority Data

Jul. 14, 1981 [IT] Italy ............................. 67972 A/81

[51] Int. Cl.³ .............................................. A61F 1/22
[52] U.S. Cl. ....................................... 3/1.5; 137/527; 137/527.8
[58] Field of Search .................... 3/1.5; 137/527, 527.8

[56] References Cited

U.S. PATENT DOCUMENTS 3,476,143 11/1969 Kaster ................................... 3/1.5 X
4,240,161 12/1980 Huffstutler, Jr. et al. ............... 3/1.5
4,308,624 1/1982 Klawitter .................................. 3/1.5

Primary Examiner—Ronald L. Frinks
Attorney, Agent, or Firm—Sughrue, Mion, Zinn, Macpeak and Seas

[57] ABSTRACT

The prosthesis comprises an annular frame and a disc-shaped obturator which is coupled to the frame and is pivotable, under the action of the blood flow, between an open annular position and a closed angular position, so as to allow the flow of blood through the aperture of the annular frame in one direction and the interruption of the flow in the opposite direction, respectively. The obturator is coupled to the frame in such a way that, in the open position, it may orient itself in a direction substantially perpendicular to the plane of the frame. The side of the obturator which faces away from the central axis of the annular frame in the open angular position is defined, at least in its peripheral part, by a surface which is generated by the rotation, about the central axis of the obturator, of a curve the locus of the centers of curvature of which lies on the opposite side of this curve from a curve which generates, by rotation around the central axis, a surface defining the other side of the obturator.

1 Claim, 7 Drawing Figures

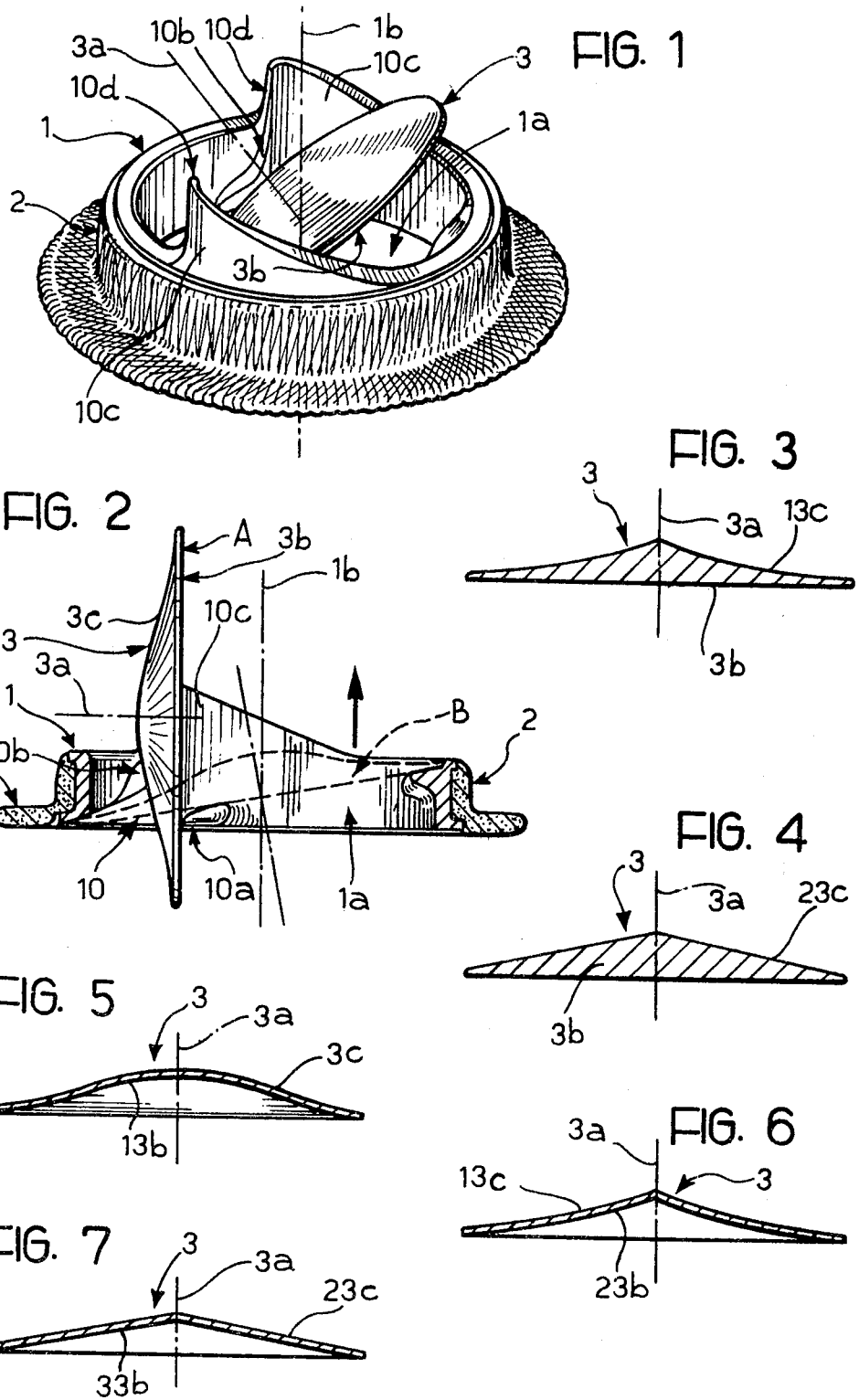

HEART VALVE PROSTHESIS

The present invention relates to heart valve prostheses, and is particularly concerned with a prosthesis comprising an annular frame, a disc-shaped obturator, and means for coupling the obturator to the annular frame which enable the obturator to rotate about its central axis and to orient itself about one of its chordal axes, under the action of the blood flow, between an open angular position and a closed angular position, so as to allow the flow of blood through the aperture of the annular frame in one direction and the interruption of the flow in the opposite direction, respectively.

In prosthetic heart valves of the aforesaid type, there is the problem of reproducing the fluid dynamic characteristics of natural heart valves, which are marked by a very low pressure gradient and the absence of areas of turbulent flow, vortices or stasis in the blood flow.

The pressure gradient across the prosthetic valve is directly related to heart activity, while irregularities of the blood flow through the prosthesis may cause haemolysis, thrombosis and changes in the characteristics of the blood medium.

In prosthetic heart valves of the aforesaid type produced according to the prior art, the obturator is in the form of a substantially flat disc which is coupled to the annular frame in such a manner that, when in the open angular position, it normally forms an angle of between 60° and 80° with the plane of the frame.

Thus, when the blood flow is reversed, the pressure exerted by the blood flow on the side of the disc which is opposite the central axis of the annular frame causes the obturator to return to the closed position, in which the obturator interrupts the flow of blood through the prosthesis.

The limitation of the opening angle of the obturator to 60°–80°, as stated above, causes the obturator to partially obstruct the aperture of the annular frame in the open position, impeding the flow of blood through the prosthesis and increasing the pressure gradient across the prosthesis.

Furthermore, in the open position, the obturator acts as a deflector of the blood flow and encourages the formation of turbulence and vortices, particularly around its peripheral parts which serve respectively as an inlet edge and an outlet edge of the obturator in the blood flow.

The object of the present invention is to provide a heart valve prosthesis of the type specified above without the above-mentioned drawbacks.

In order to achieve this object, the present invention relates to a heart valve prosthesis of the type specified above, characterised in that the coupling means are such as to enable the obturator to orient itself substantially perpendicular to the plane of the frame in the open position, and in that the side of the obturator which faces away from the central axis of the annular frame in the open angular position is defined, at least in its peripheral part, by a surface which is generated by rotation, about the central axis of the obturator, of a curve the locus of the centres of curvature of which lies on the opposite side of said curve from a curve which generates, by rotation about said central axis, a surface defining the other side of the obturator.

By virtue of this characteristic, the flow of blood through the prosthesis is not obstructed appreciably by the obturator in its open position.

In the open angular position, the peripheral part of the obturator lies in a plane which is substantially parallel to the lines of the blood flow through the central aperture of the frame. The formation of any turbulence, vortices or other irregularities in the blood flow is thus avoided.

The invention will now be described, purely by way of non-limiting example, with reference to the attached drawings, in which:

FIG. 1 is a perspective view of a heart valve prosthesis according to the invention;

FIG. 2 is an axial section of the prosthesis of FIG. 1, and

FIGS. 3 to 7 are axial sections showing respective variants of an element shown in FIGS. 1 and 2.

FIG. 1 shows, in its entirety, an annular frame 1 of biocompatible material with a central aperture 1a and with a central axis 1b. The outer surface of the annular frame 1 has a textile covering 2 made from a biocompatible synthetic yarn.

The covering 2 acts as a sutural element which enables the prosthesis to be applied to the heart muscle after removal of the original valve membranes.

Coupled to the annular frame 1 is a disc-shaped obturator 3 which has rotational symmetry about a central axis 3a and is pivotable relative to the frame 1 between an open angular position, shown by the continuous line A in FIG. 2, and a closed angular position, shown by the broken lines B in the same Figure.

In the open angular position A, the obturator 3 allows blood to flow through the central aperture 1a of the annular frame 1 in the direction shown by the arrow in FIG. 2.

In the closed angular position B, the obturator 3 interrupts the flow of blood in the opposite direction through the aperture 1a.

The obturator 3 is coupled to the annular frame 1 with a slight radial clearance which allows the obturator 3 to rotate about its central axis 3a, in addition to the angular orienting movement between the open position A and the closed position B, so that the mechanical stresses and phenomena of wear which appear during the operation of the prosthesis are uniformly distributed around the edge of the obturator 3.

The radial clearance between the obturator 3 and the annular frame 1, when the obturator is in the closed position B, enables a small reflux of blood through the aperture 1a so as to avoid the formation of areas of stasis.

In accordance with known principles, the obturator 3 is coupled to the annular frame 1 by coupling means, generally indicated 10, which allow the obturator 3 to orient itself angularly about an axis lying on a chord which is approximately equidistant from the central axis 1b and the peripheral edge of the annular frame 1.

The orientation axis of the obturator 3 may be displaced during the angular movement between the open position A and the closed position B when, during this movement, the obturator 3 effects a slight translational movement in its own plane. For the sake of simplicity, this axis will be defined as the "chordal axis" in the claim which follows.

In the illustrated embodiment, the coupling means 10 comprise a pair of first protuberances 10a and a pair of second protuberances 10b, which project from the frame 1 into the aperture 1a, and triangular projections 10c which extend from the annular frame 1 in an approximately axial direction relative to the frame 1.

The first protuberances 10a engage a side 3b of the obturator 3, which faces towards the central axis 1b of the frame 1 in the open position A.

The second protuberances 10b engage the other side 3c of the obturator 3, which faces away from the central axis 1b in the open position A.

Thus, each first protuberance 10a forms, with the respective second protuberance 10b, a fork-shaped element which embraces a peripheral part of the obturator 3 and, in the manner of a fulcrum, guides the orienting movement of the obturator 3 relative to the frame 1.

The triangular projections 10c are curved slightly towards the inside of the annular frame 1, and those of their faces which are turned towards the central axis 1b of the frame 1 have a concavity complementary to the peripheral curvature of the obturator 3, so that the obturator 3 is retained by the annular frame 1, being coupled thereto in a manner which permits the orientation.

The triangular projections 10c have edges 10d which face the central axis 1b and are curved slightly towards the inside of the annular frame 1. The curved edges 10d curtail the opening stroke of the obturator 3 at position A where the obturator 3 is substantially perpendicular to the plane of the annular frame 1.

In the embodiment illustrated in FIGS. 1 and 2, the side 3c of the obturator 3 is defined, in its central part, by a convex surface and, in its peripheral part, by a surface which is generated by rotation, about the central axis 3a of the obturator, of a curve the locus of the centres of curvature of which lies on the opposite side of this curve from a curve (straight in the example shown in FIGS. 1 and 2) which generates, by rotation around the central axis 3a, a surface defining the other side 3b of obturator 3.

The two generatrix curves must be mutually positioned in a plane which is radial to the obturator (the plane of rotation).

In the variant illustrated in FIG. 3, the side 13c of the obturator 3 which faces away from the central axis 1b of the annular frame 1 in the open angular position A is defined entirely by a rotation surface of the aforesaid type. Thus, the obturator shown in FIG. 3 differs from that shown in FIGS. 1 and 2 only in that the central part of the side 13c in FIG. 3 has a more or less pointed convexity, in contrast to the rounded convexity characteristic of the central part of the side 3b of the obturator 3 shown in FIGS. 1 and 2.

In the variant shown in FIG. 4, the side 23c corresponding to sides 3c, 13c of FIGS. 1, 2 and 3 is defined by a conical surface where the locus of the centres of curvature lies virtually at infinity.

In the variants illustrated in FIGS. 5, 6 and 7, the surfaces defining the sides 3c, 13c, 23c of the obturator 3 are identical to the surfaces which define the corresponding sides of the obturators illustrated in FIGS. 2, 3 and 4 respectively.

In the obturators 3 shown in FIGS. 5, 6 and 7, the sides 13b, 23b, 33b which face the central axis 1c of the annular frame 1 in the open position A are defined by surfaces which are complementary to the surfaces of the sides 3c, 13c and 23c respectively, thus giving the obturator a more or less constant thickness in all parts.

The operation of the valve prosthesis according to the invention, which will now be described with reference to the embodiment shown in FIGS. 1 and 2, is controlled by the action of the blood flow on the obturator 3.

When the obturator 3 is in the open angular position A and the blood is flowing through the central aperture of the annular frame 1 in the direction indicated diagrammatically by the arrow in FIG. 2, the obturator 3 lies in a plane which is substantially perpendicular to the plane of the frame 1 and its central axis 3a is substantially perpendicular to the central axis 1b of frame 1.

In these conditions, the obturator 3 offers minimal resistance to the blood flow. The peripheral edge of obturator 3 lies in a plane which is substantially parallel to the axis 1b and the lines of blood flow. In this manner, the formation of turbulence, vortices and other irregularities in the blood flow is kept to a minimum. By virtue of the particular geometry of side 3c, the deviation of the flow lines caused by obturator 3 is gradual, and their parallelism is restored immediately downstream of the obturator.

When the blood flow direction is reversed with respect to the direction shown by the arrow in FIG. 2, the flow of blood causes pressure to be exerted on the surface of the obturator 3, and the resultant force acts relative to the chordal axis with a momentum which causes the obturator 3 to pivot towards the closed position B.

When the heart muscle causes a further reversal in direction of the blood flow, the blood stream impinges on the side 3b of the obturator 3 which faces the aperture 1a in the closed position B, and the obturator 3 is thereby returned to its open position A.

Naturally, while the principle of the invention remains unchanged, the details of construction and forms of embodiment may be varied videly from that described and illustrated. In particular, the pivoting of the obturator 3 to the annular frame 1 may be effected according to any of the methods known in the art without departing from the scope of the present invention.

We claim:

1. A heart valve prosthesis comprising an annular frame, a disc-shaped obturator, and means for coupling the obturator to the annular frame which allow the obturator to rotate around its central axis and to orient itself about one of its chordal axes, under the action of the blood flow, between an open angular position and a closed angular position so as to allow the free flow of blood through the aperture of the annular frame in one direction and the interruption of the flow in the opposite direction, respectively, wherein said coupling means are such as to enable the obturator to orient itself perpendicular to the plane of the frame in the open angular position, and the side of the obturator which faces away from the central axis of the annular frame in the open angular position is defined, at least over a major portion of its peripheral part, by a surface which is generated by rotation about the central axis of the obturator, of a curve, the locus of centres of curvature of which lies at a finite distance on the opposite side of said curve from a curve which generates, by rotation about said central axis of the obturator, a surface defining the other side of the obturator, whereby, when the obturator is in the open angular position, blood flowing through the aperture of the annular frame is smoothly deflected over and around the obturator.

* * * * *